United States Patent [19]
Nakamura-Craig

[11] Patent Number: 5,801,171
[45] Date of Patent: Sep. 1, 1998

[54] USE OF 3, 5-DIAMINO-6-(2,3-DICHLOROPHENYL)-1, 2, 4-TRIAZINE ISETHIONATE FOR THE TREATMENT AND PREVENTION OF DEPENDENCE; TOLERANCE AND SENSITIZATION OF DRUGS

[75] Inventor: Meire Nakamura-Craig, Beckenham, Great Britain

[73] Assignee: Glaxo Wellcome Inc, Research Triangle Park, N.C.

[21] Appl. No.: 347,480

[22] PCT Filed: Jun. 11, 1993

[86] PCT No.: PCT/GB93/01243

§ 371 Date: Dec. 6, 1994

§ 102(e) Date: Dec. 6, 1994

[87] PCT Pub. No.: WO93/25207

PCT Pub. Date: Dec. 23, 1993

[30] Foreign Application Priority Data

Jun. 12, 1992 [GB] United Kingdom .................... 9212495
Apr. 27, 1993 [GB] United Kingdom .................... 9308654

[51] Int. Cl.$^6$ ...................................... A01N 43/64
[52] U.S. Cl. .......................... 514/242; 514/810; 514/811; 514/812; 514/813
[58] Field of Search ............................ 514/242, 810, 514/811, 812, 813

[56] References Cited

FOREIGN PATENT DOCUMENTS

| 0021121 | 1/1981 | European Pat. Off. . |
| 0247892 | 12/1987 | European Pat. Off. . |
| 0459829 | 12/1991 | European Pat. Off. . |

OTHER PUBLICATIONS

Leach et al: "Neurochemical and Behavioural Aspects of Lamotrigine," *EPILEPSIA*, vol. 32, No. SUP2, 1991, pp. S4–S8.

Oonnell et al: "The Effect of Lamotrigine Upon Development of Cortical Kindled Seizures in the Rat," *Neuropharmacology*, vol. 30, No. 3, Mar. 1991, pp. 253–258.

Weiss et al: "Chronic Carbamazepine Inhibits the Development of Local Anaesthetic Seizures Kindled by Cocaine and Lidocaine," vol. 497, No. 1, 11 Sep. 1989, pp. 72–79.

*The Merck Index*, Eleventh Edition, 1989, "Lamotrigine", p. 844.

*Primary Examiner*—John M. Cooney, Jr.
*Attorney, Agent, or Firm*—Nixon & Vanderhye

[57] ABSTRACT

3,5-diamino-6-(2,3-dichlorophenyl)-1,2,4-triazine and its pharmaceutically and veterinarily acceptable salts have activity in (a) preventing or reducing dependence on, and (b) preventing or reducing tolerance or reverse tolerance to, a dependence inducing agent such as an opioid, a central nervous system depressant, a psychostimulant or nicotine.

11 Claims, 9 Drawing Sheets

USE OF 3, 5-DIAMINO-6-(2,3-DICHLOROPHENYL)-1, 2, 4-TRIAZINE ISETHIONATE FOR THE TREATMENT AND PREVENTION OF DEPENDENCE; TOLERANCE AND SENSITIZATION OF DRUGS

The present invention relates to the use of 3,5-diamino-6-(2,3-dichlorophenyl)-1,2,4-triazine and its pharmaceutically and veterinarily acceptable acid addition salts in therapy.

EP-A-0 021 121 describes a group of triazine compounds, including 3,5-diamino-6-(2,3-dichlorophenyl)-1,2,4-triazine, and acid addition salts thereof, which are active in the treatment of disorders of the central nervous system, for example psychiatric and neurological disorders, and which are particularly useful as anticonvulsants, for instance in the treatment of epilepsy. The compounds are non-depressant and are therefore advantageous compared with depressant antiepileptics such as phenobarbitone. EP-A-0 247 892 describes 3,5-diamino-6-(2,3-dichlorophenyl)-1,2,4-triazine isethionate, a particularly preferred salt owing to its good solubility.

In mechanistic studies, 3,5-diamino-6-(2,3-dichlorophenyl)-1,2,4-triazine has been shown at anticonvulsant brain concentrations to inhibit the release of excitatory amino acids, principally glutamate (Leach, M. J. et al. (1986), *Epilepsia* 27, 490–497; Zhu, S. G. and McGee, E. G. (1990), *Neurosci. Lett.* 112, 348–351). Glutamate functions as an important neurotransmitter in the mammalian central nervous system and has been identified as having specific actions in the peripheral nervous system. The known anticonvulsant effect of this compound has therefore been ascribed to its ability to act as an inhibitor of glutamate release.

A number of currently available drugs that produce effects on mood, thought or feeling have a well-recognized potential for addiction and misuse; see for example Chapter 22 in Goodman and Gilman's "The Pharmacological Basis of Therapeutics", eighth edition, McGraw-Hill, Inc. (1992). One of the hazards in the use of such a drug is that some individuals eventually develop a dependence on it; they continue to take it in the absence of medical indications, often despite adverse social and medical consequences, and behave as though its effects were essential for continued well-being. The intensity of this need may vary from a mild desire to a craving or compulsion to use the drug and, when its availability is uncertain, individuals may exhibit a preoccupation with its procurement.

A further aspect of drug use and misuse is drug tolerance, which is manifested as a reduction in a particular effect upon repeated exposure to a drug at constant dose, or the need for an increased dose of a drug to maintain a given effect. A related phenomenon is reverse tolerance (sensitisation), whereby the repeated administration of a given drug produces an increase in a particular effect.

No successful clinical management yet exists for drug dependence or drug tolerance, despite the significant problems caused by each for the individual and for society. There is therefore a need for effective ways of treating drug dependence and tolerance.

It has now surprisingly been found that 3,5-diamino-6-(2,3-dichlorophenyl)-1,2,4-triazine and its pharmaceutically and veterinarily acceptable acid addition salts are effective in controlling drug dependence and tolerance. Accordingly, the present invention provides the use of 3,5-diamino-6-(2, 3-dichlorophenyl)-1,2,4-triazine or a pharmaceutically or veterinarily acceptable acid addition salt thereof in the preparation of a medicament for

(a) preventing or reducing dependence on, or
(b) preventing or reducing tolerance or reverse tolerance to, a dependence-inducing agent.

3,5-Diamino-6-(2,3-dichlorophenyl)-1,2,4-triazine will hereinafter be referred to as compound A. Compound A and its acid addition salts will be referred to collectively as the present compounds.

Suitable acid addition salts of compound A include those formed with either organic or inorganic acids. Such acid addition salts will normally be pharmaceutically and veterinarily acceptable. Examples of such salts include those formed with hydrochloric, sulphuric, citric, tartaric, phosphoric, lactic, pyruvic, acetic, succinic, fumaric, maleic, methanesulphonic, ethanesulphonic, oxaloacetic or isethionic acid. The salt with isethionic acid is preferred since it possesses particularly good solubility.

The present compounds may be prepared by a process which comprises cyclising a compound of formula (II):

and, if desired, converting compound A thus obtained into a pharmaceutically or veterinarily acceptable acid addition salt.

The cyclisation is typically carried out by heating the compound of formula (II) under reflux in an alkanol, preferably a $C_{1-4}$ alkanol, for example methanol or ethanol, in the presence of a strong base, for example potassium hydroxide. The process may, for instance, be carried out as described in Example 1 of EP-A-0 021 121. The optional subsequent step of converting the compound A into an acid addition salt is performed by a conventional method, for example by treatment with the appropriate acid at ambient temperature. The salt with isethionic acid may be prepared, for instance, as described in EP-A-0 247 892, in particular in Example 3.

The starting compound of formula (II) may be prepared by the method described in U.S. Pat. No. 3,637,688.

The term "dependence-inducing agent" as used herein refers to any substance on which an individual can become dependent, including pharmaceuticals, alcohol, nicotine and volatile solvents. Particular examples of dependence-inducing agents are (Goodman and Gilman, loc. cit):

(1) opioids, for example heroin and morphine
(2) central nervous system (CNS) depressants, for example alcohol (i.e. ethanol), barbiturates and benzodiazepines;
(3) psychostimulants, for example amphetamine and congeners such as 3,4-methylenedioxymethylamphetamine (MDMA, "ecstasy"), and cocaine;
(4) nicotine and tobacco;
(5) cannabinoids, for example from use of cannabis (hashish, marijuana);
(6) psychedelics (hallucinogens, psychotomimetics, psychotogens);
(7) arylcyclohexylamines;
(8) inhalants, for example anaesthetic gases such as nitrous oxide and volatile solvents such as diethylether.

Preferred examples of dependence-inducing agents in the context of the present invention include morphine, ethanol, cocaine and nicotine.

One definition of dependence is the need for continued exposure to a drug so as to avoid a withdrawal syndrome (manifested as physical and/or psychological disturbances) when the drug is withdrawn. Dependence is considered a priori to result from adaptive changes that develop in body tissues in response to repeated drug exposure. Although there has traditionally been a distinction between psychological and physical dependence, this is now though to be somewhat artificial since both are mediated by neural mechanisms (Nestler, E. J., *J. Neurosci.* July 1992, 12(7): 2439–2450).

The term drug dependence as used herein (Goodman and Gilman, loc. cit) refers to a syndrome in which the use of a drug is given a much higher priority than other behaviours that once had higher value; in its extreme form, it is associated with compulsive drug-using behaviour. Drug dependence is commonly associated with the development of physical dependence, which as used herein refers to an altered physiological state (neuroadaptation), produced by the repeated administration of a drug, which necessitates continued administration of the drug to prevent the appearance of a withdrawal or abstinence syndrome characteristic of that particular drug.

As discussed by Nestler, loc. cit, physical dependence was in the past part of the definition of addition, otherwise defined as the compulsive use of a drug despite adverse consequences. However, many drugs with no abuse potential, e.g. β-adrenergic antagonists, clonidine and tricyclic antidepressants, can produce marked physical symptoms on withdrawal. In contrast, individuals dependent on certain drugs such as marijuana and cocaine may experience little or no physical withdrawal syndrome when drug exposure ceases.

Compound A has activity in animal models of dependence on, and tolerance and reverse tolerance to, dependence-inducing agents as described in Examples 1 to 7 which follow. The present invention therefore provides a method of (a) preventing or reducing dependence on, or (b) preventing or reducing tolerance or reverse tolerance to, a dependence-inducing agent, which method comprises administering to a mammal in need of such treatment a therapeutically effective amount of one of the present compounds. In this way dependence on, and tolerance and reverse tolerance to, a dependence-inducing agent can be controlled. The condition of a human or animal may thus be improved.

The present compounds have utility in treating drug dependence and tolerance. They may therefore be used to treat drug dependence or physical dependence as hereinbefore defined. They may also be used to treat tolerance, or reverse tolerance, to a drug. The compounds are effective in preventing dependence, tolerance or reverse tolerance from developing. They are also effective in reducing dependence, tolerance or reverse tolerance which has already become established in a human being or animal subject.

An inherent feature of physical dependence as above defined is the appearance of physical symptoms upon withdrawal. In one embodiment of the invention, therefore, the present compounds are used to treat, i.e. to reduce or eliminate, the symptoms associated with withdrawal from a dependence-inducing agent. Such withdrawal symptoms include in particular anxiety, diarrhoea, fluctuations in body temperature, disturbed sleep patterns and behavioural symptoms such as tremors, hyperactivity and ataxia. The present compounds may, for example, be used to treat behavioural symptoms of withdrawal from a dependence-inducing agent, for example ethanol, or to reduce anxiety induced by withdrawal from a dependence-inducing agent such as nicotine. The present compounds may also be used to treat drug dependence where there is not necessarily an associated physical dependence, such as described above for marijuana and cocaine.

In one embodiment of the invention one of the present compounds is administered concomitantly with a dependence-inducing agent. Administration of the two agents may thus be simultaneous or sequential.

In accordance with the present invention, the present compounds may be used in so-called substitution treatment of physical dependence. Substitution treatment is based on the phenomenon of cross-dependence, whereby one drug can suppress the manifestations of physical dependence produced by another whilst maintaining the physically dependent state (see, for example, Goodman and Gilman, loc. cit.) If a short-acting drug is replaced over several days by a longer-acting drug with which it is cross-dependent, discontinuation then produces withdrawal symptoms characteristic of the longer-acting drug. Thus, for example, substitution treatment of heroin addiction involves replacing heroin by methadone.

The benefit of substitution treatment is that withdrawal symptoms associated with the longer-acting drug will generally be less severe (but more protracted) than those that occur with the short-acting drug. However, these less severe withdrawal symptoms can be further reduced or eliminated by administering one of the present compounds concomitantly with the longer-acting drug.

Dependence on a first dependence-inducing agent may thus be prevented or reduced by the concomitant administration of one of the present compounds and a second dependence-inducing agent with which the first dependence-inducing agent is cross-dependent. Typically the second dependence-inducing agent is longer acting than the first dependence-inducing agent. In one embodiment of the invention, dependence on heroin or on morphine may be treated by the concomitant administration of methadone and one of the present compounds, e.g. compound A.

The activity of the present compounds is particularly surprising because, as demonstrated in the Comparative Examples, carbamazepine (another known anticonvulsant) is not effective in treating physical dependence. This suggests that the activity of the present compounds in preventing and reducing dependence, tolerance and reverse tolerance is not attributable to their anticonvulsant properties.

The present compounds are non-toxic at prophylactically and therapeutically effective doses. They can be administered in a variety of dosage forms including those for oral, rectal, parenteral (such as subcutaneous, intramuscular and intravenous) and buccal (including sublingual) administration.

The present compounds may be administered in any of the above dosage forms at a dose of from 1 mg/kg to 30 mg/kg per day, for example from 5 mg/kg to 10 mg/kg per day. The dose range for adult human beings will depend on a number of factors including the age, weight and condition of the patient and the administration route. A dose of 5 mg/kg to 10 mg/kg by the oral route is particularly suitable. A typical dosage regimen is from 20 mg to 2400 mg per day, typically from 350 mg to 1050 mg per day, preferably from 600 mg to 800 mg per day. It may in some situations be advantageous, since the present compounds are long-acting, to administer an initial dose of 70 mg to 2400 mg on the first day of treatment and then a lower dose of 20 mg to 1200 mg on subsequent days (all weights calculated as the base).

The present invention further provides a composition comprising a pharmaceutically or veterinarily acceptable carrier or diluent and, as an active principle, one of the present compounds. Preferably the composition comprises a pharmaceutically accepter carrier or diluent, a dependence-inducing agent and one of the present compounds. The composition can be prepared using conventional methods, e.g. by admixing, and administered in a pharmaceutically acceptable form. The invention also provides a dependence-inducing agent in admixture with one of the present compounds.

For oral administration, fine powers or granules containing diluting, dispersing and/or surface-active agents may be presented in a draught, in water or a syrup, in capsules or sachets in the dry state, in a non-aqueous suspension wherein suspending agents may be included, or in a suspension in water or a syrup. Where desirable or necessary, flavouring, preserving, suspending, thickening, or emulsifying agents can be included. When a suspension is prepared in water according to the present invention at least one of such agents will be present.

Other compounds which may be included by admixture are, for example, medically inert ingredients, e.g. solid and liquid diluents, such as lactose, dextrose, saccharose, cellulose, starch, or calcium phosphate, for tablet or capsules; olive oil or ethyl oleate for soft capsules; water or vegetable oil for suspensions or emulsions; lubricating agents such as silica, talc, stearic acid, magnesium or calcium stearate and/or polyethylene glycols; gelling agents, such as colloidal clays; thickening agents, such as gum tragacanth or sodium alginate; binding agents such as starches, arabic gums, gelatin, methylcellulose, carboxymethylcellulose or polyvinylpyrrolidone; disintegrating agents such as starch, alginic acid, alginates or sodium starch glycolate; effervescing mixtures; dye-stuffs; sweeteners; wetting agents such as lecithin, polysorbates or laurylsulphates; and other therapeutically acceptable accessory ingredients, such as humectants, preservatives, buffers and antioxidants, which are known additives for such formulations.

Liquid dispersions for oral administration may be syrups, emulsions and suspensions. The syrups may contain a carrier, for example, saccharose or saccharose with glycerol and/or mannitol and/or sorbitol. In particular a syrup for diabetic patients can contain as carriers only products, for example sorbitol, which do not metabolise to glucose or which only metabolise a very small amount to glucose. The suspensions and the emulsions may contain a carrier, for example a natural gum, agar, sodium alginate, pectin, methylcellulose, carboxymethylcellulose or polyvinyl alcohol.

Suspensions or solutions for intramuscular injection may contain, together with the active compound, a pharmaceutically acceptable carrier such s sterile water, olive oil, ethyl oleate, glycols such as propylene glycol, and if desired, a suitable amount of lidocaine hydrochloride. Solutions for intravenous injection or infusion may contain a carrier, for example, sterile water which is generally Water for Injection. Preferably, however, they may take the form of a sterile, aqueous, isotonic saline solution. Alternatively, the present compounds may be encapsulated within liposomes.

The free base or an acid addition salt thereof may also be administered in its pure form unassociated with other additives, in which case a capsule, sachet or tablet, is the preferred dosage form.

Tablets and other forms of presentation provided in discrete units conveniently contain a daily dose, or an appropriate fraction thereof, of one of the present compounds. For example, units may contain from 5 mg to 500 mg, but more usually from 10 mg to 250 mg of one of the present compounds, calculated as the base.

The invention is further illustrated in the Examples which follow.

In the accompanying drawings.

| Column | |
|---|---|
| 1: | saline (i.p) + celacol |
| 2: | saline (i.p) + compound A (20 mg/kg p.o) |
| 3: | saline (i.p) + cocaine (10 mg/kg p.o) |
| 4: | cocaine (10 mg/kg i.p) + celacol |
| 5: | cocaine (10 mg/kg i.p) + compound A (20 mg/kg p.o) |
| 6: | cocaine (10 mg/kg i.p) + compound A (single dose only of 20 mg/kg p.o. on day 8) |

EXAMPLE 1

Testing of a compound A on the development of morphine tolerance in a rat tail flick model Animals Male Wistar-strain rats were supplied by Charles River U.K. Ltd one week prior to use. They were housed in groups of 5 under controlled environmental conditions, ambient temperature 20°±1° C., relative humidity 55% and photoperiod 07.00–19.00 h. Pelleted diet and drinking water were available at all times. At the time of use the rats weight 140–190 g.

Materials

Test compounds were prepared as suspensions in 0.25% methylcellulose (celacol) by ball-milling overnight at 4° C. using a Pascall ball-mill. Further dilution was carried out in celacol as required to give a range of doses. Morphine hydrochloride was prepared as a solution in 0.85% saline to give an equivalent of 10 mg/kg of the base.

Procedure

Groups of 5 to 10 animals were given celacol (p.o.) and saline (s.c) (C+S in FIG. 1), celacol (p.o.) and morphine (10 mg/kg s.c) (C+M) or compound A (5 mg/kg p.o.) and morphine (10 mg/kg s.c) (A+M) twice daily at 09.00 and 17.00 for 4 days. Celacol and compound A were each administered 1 hour prior to the morphine. On day 5 all animals were challenged with 3.7 mg/kg of morphine, equivalent to an $ED_{90}$ in normal animals.

The animals were tested in the tail flick model described by D'Amour, F. E. and Smith, D. L. in J. Pharmacol. Exp. Ther. 72: 74–79 (1941). In this test animals respond to a focused heat stimulus by "flicking" or removing their tail from the path of the stimulus, thereby exposing a photocell located in the apparatus immediately below the tail. The time for the animal to flick or remove the tail (reaction time, sec) is then recorded.

Figure 1:
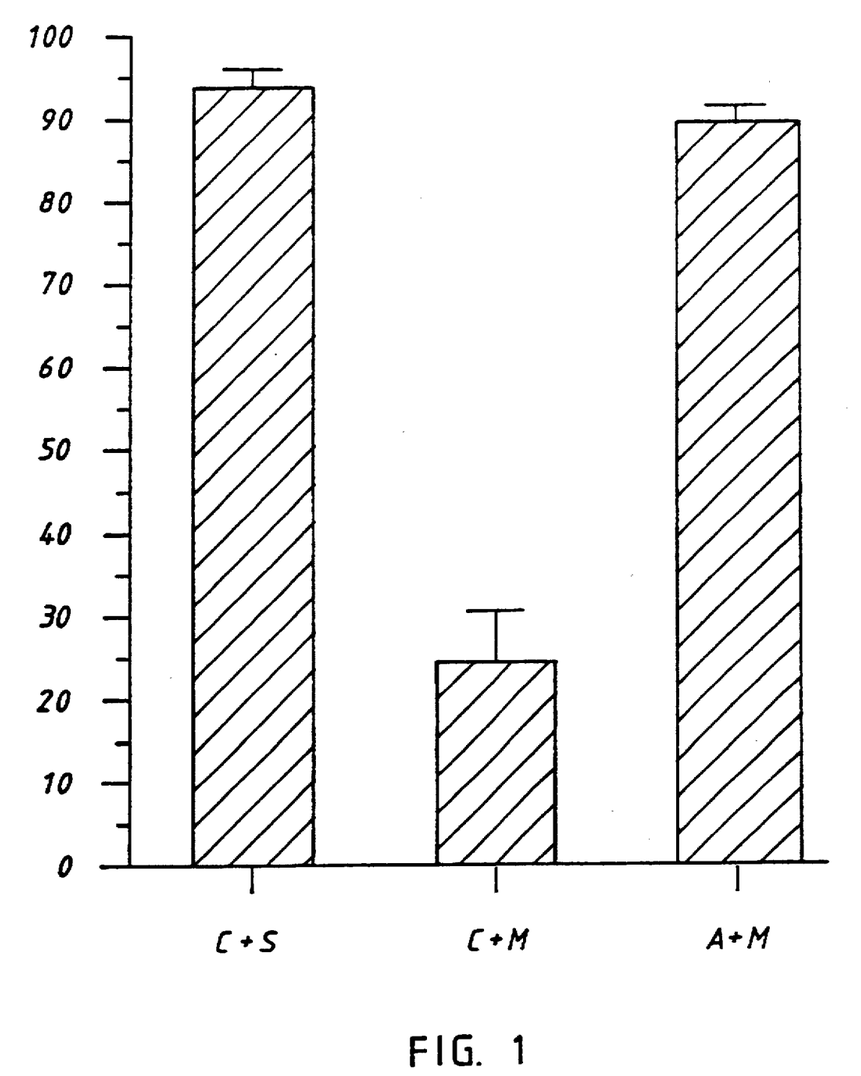
FIG. 1 shows the mean of % analgesis (±s.e.m.) (y axis) for celacol and saline (control, C+S), celacol and morphine (C+M) and compound A and morphine (A+M) in the test of Example 1.

30 minutes after morphine challenge in the present study, tail flick reaction times to the focused beam of radiant heat were measured. A cut-off time of 10 seconds was used to avoid tissue damage to the tail. The results are presented in FIG. 1 as index of analgesis (%) calculated using the following formula:

$$\frac{\text{reaction time after treatment} - \text{predose reaction time}}{\text{cut off (10 sec)} - \text{predose reaction time}} \times 100$$

Thus 100% analgesia is observed in rats that do not respond to heat stimulus in 10 sec.

In FIG. 1 significant difference from C+S is shown as $p<0.001$ (Student's test). Compound A clearly attenuated the development of morphine tolerance at a dose which does not significantly affect the analgesic effect of the morphine.

EXAMPLE 2

Testing of compound A on the analgesic action of morphine in morphine-tolerant rats Animals and materials were as describe in Example 1.

Procedure

Figure 2:
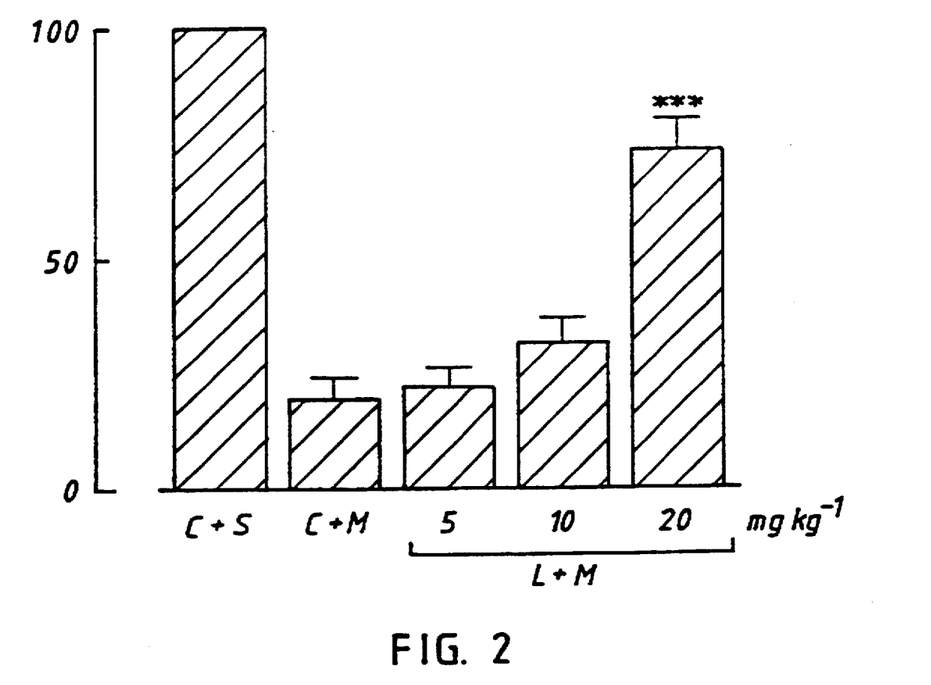
FIG. 2 shows the mean of % analgesia (y axis) for celacol and saline (control, C+S), celacol and morphine (C+M) and compound A at doses of 5, 10 and 20 mg/kg with morphine (A+M) in the test of Example 2.

Groups of 5 to 10 animals were given morphine (10 mg/kg s.c.) twice daily, at 09.00 and 17.00, for four days to induce morphine tolerance. On days 5, 6 and 7 when tolerance had developed the treatment was continued, but the rats were also given celacol (p.o.) (C+M in FIG. 2) or compound A (5, 10 or 20 mg/kg p.o.) (A+M in FIG. 2) 1 hour prior to each dose of morphine.

On day 8 the tail flick test described in Example 1 was performed 1 hour after a further dose of morphine (10 mg/kg s.c.). The results are presented in FIG. 2 as mean±s.e.m. of % analgesia (N=10). Significant difference from C+M is shown as ***$p<0.001$ (Student's test). Compound A clearly caused a dose-dependant reduction in the tolerance which the rats had developed to morphine.

EXAMPLE 3

Effect of Compound A on morphine dependence in a rat withdrawal jumping model

Animals and materials were as described in Example 1.

Procedure

Groups of 5 to 10 animals were given celacol and morphine (10 mg/kg s.c.) (C+M) or compound A (5, 10 or 20 mg/kg p.o.) and morphine (10 mg/kg s.c.) for 4 days. On day 5 dosing was repeated and morphine abstinence syndrome was precipitated one hour later by administration of naloxone (2.0 mg/kg s.c.). Immediately after injection the rats were placed individually into transparent perspex cylinders 40 cm high and 19 cm internal diameter. The frequency of jumping (all 4 feet off the floor) was recorded at 2 minute intervals for 10 mins.

Figure 3:
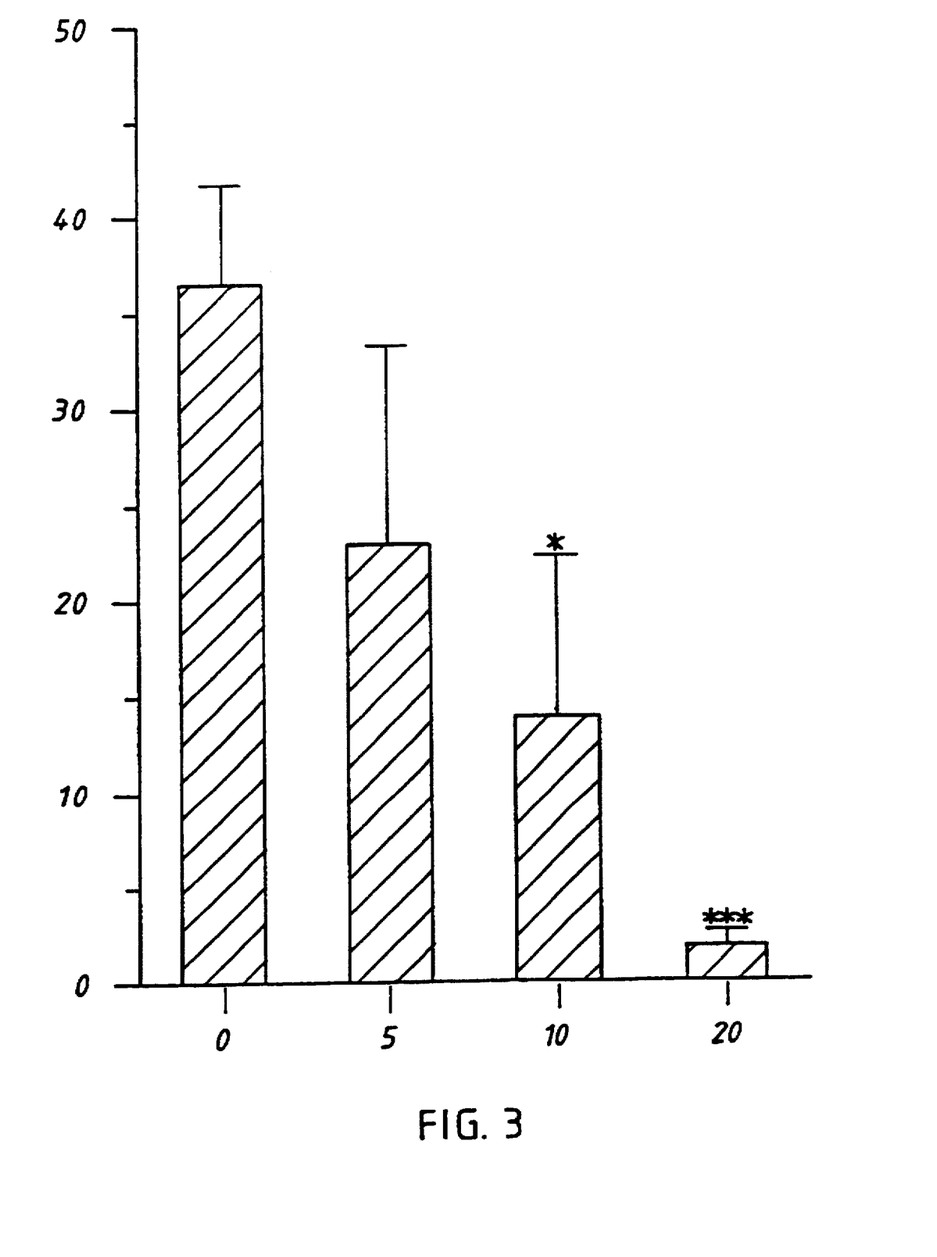
FIG. 3 shows the mean (±s.e.m.) of total numbers of jumps (n=10) for compound A at doses of 0, 5, 10 and 20 mg/kg, in the morphine withdrawal jumping test of Example 3.

The results are shown in FIG. 3 as mean±s.e.m. of total number of jumps (n=10) versus dose in mg/kg of compound A. Significant difference from control is shown as *$p<0.05$ and ***$p<0.001$ (Mann-Whitney test). The results show that compound A causes a dose-dependent reduction in the number of jumps provoked by morphine withdrawal.

EXAMPLE 4

Effect of compound A on morphine dependence in a withdrawal behavioural syndrom rat model Animals and materials were as described in Example 1.

Procedure

Figure 4:
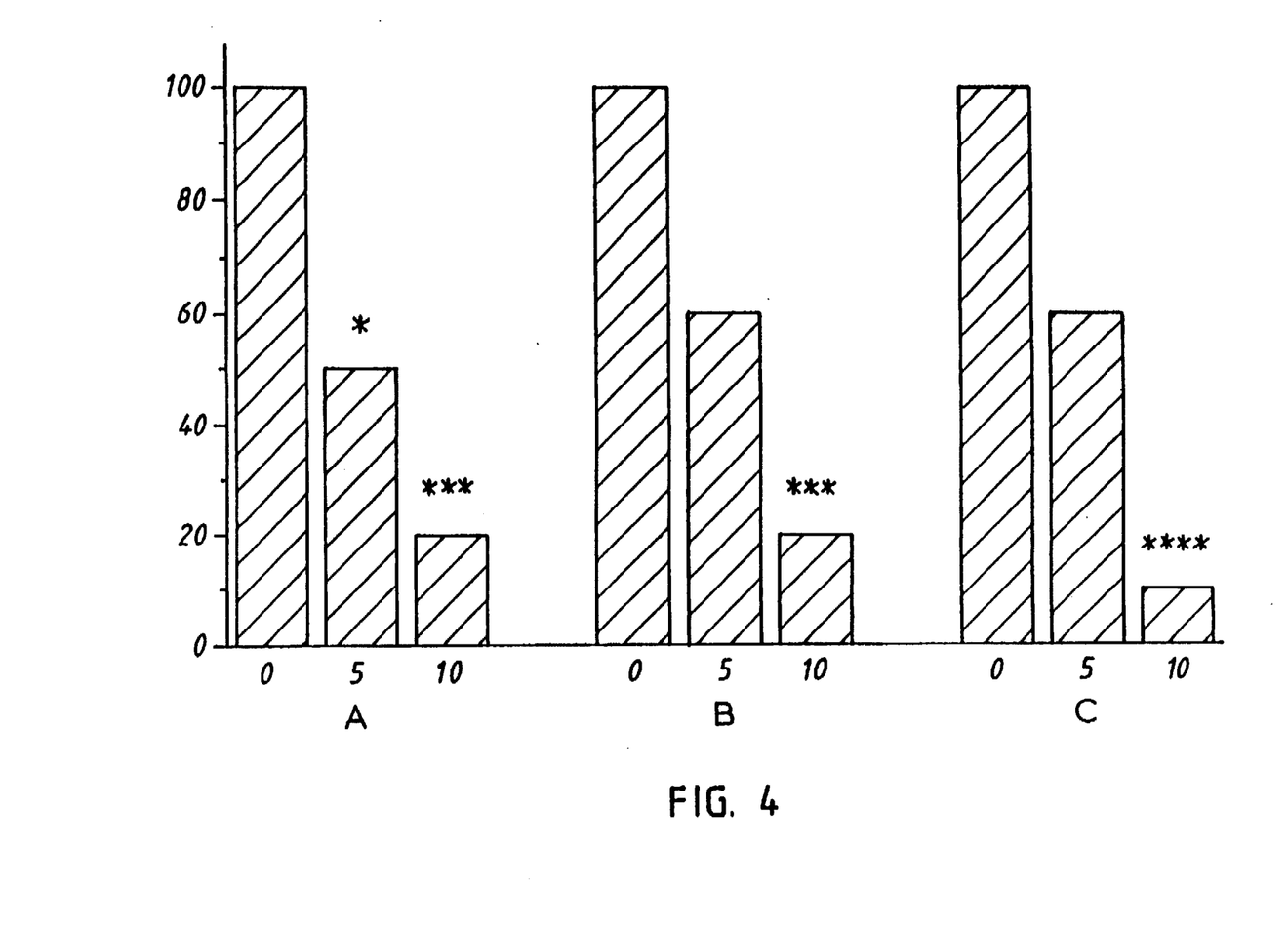
FIG. 4 shows the percentage of animals exhibiting diarrhoea effects (A), paw tremor (B) and posture/writhing effects (C) at doses of 0, 5 and 10 mg/kg of compound A in the morphine withdrawal behavioural syndrome test of Example 4.

Groups of 5 to 10 animals were given compound A (5 or 10 mg/kg p.o.) or celacol as control twice daily for 4 days, 1 hours prior to morphine administration (10 mg/kg, s.c.). On day 5 dosing was repeated and morphine abstinence syndrome was precipitated 5 hours later with naloxone (0.3 mg/kg s.c.). Immediately after injection the rats were placed individually into perspex cylinders as described for the jumping test of Example 3, and observed for the appearance of behavioural effects such sa paw tremor, "wet dog shakes", diarrhoea and changes in posture or activity for 20 mins. The results are shown in FIG. 4, presented as the percentage of animals from at least 9 per treatment group, exhibiting each of the behavioural effects observed. The treatment-related incidence of behavioural effects was compared to that of control animals using Fischer's exact probability test, with significance of difference between compound A and celacol-treated controls shown as *$p=0.02$, *$p=0.0006$, **$p=0.0001$. The results show that compound A reduces the incidence of behavioural symptoms of morphine-withdrawal in a dose-dependant fashion.

EXAMPLE 5

Effect of compound A on alcohol dependence in a withdrawal behavioural syndrome rat model Animals and materials were as described in Example 1. The rats weighed 200–250 g at the time of use.

Ethanol (20%, 5 ml per rat p.o.) was given to rats 4 times daily for 7 days, at 08.00, 13.00, 18.00 and 24.00. Compound A (10 mg/kg p.o.) or celacol as control was given on five occasions, 1 hour before the third ethanol dose on day 4 and 1 hour before the first and third doses on days 5 and 6.

8–12 hours after the last dose of ethanol the animals were observed individually on an arena for different behavioural effects of alcohol withdrawal, which were scored for severity on an arbitrary scale.

Figure 5:
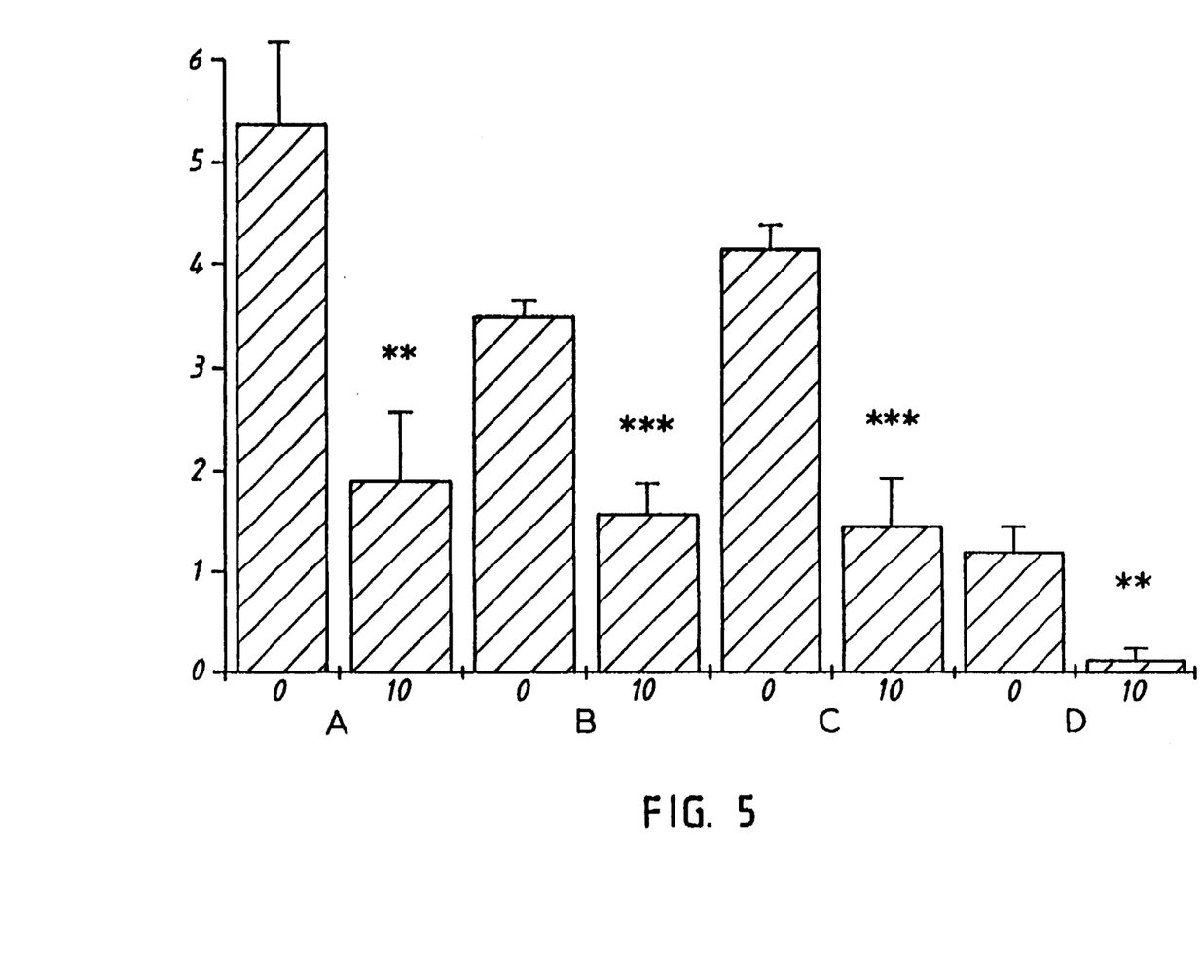
FIG. 5 shows the mean activity score (±s.e.m.) for activity (A), ataxia (B), irritability (C) and tremor (D) in rats treated with compound A at 0 and 10 mg/kg p.o. in the alcohol withdrawal behaviour test of Example 5.

The results are shown in FIG. 5 where the average score (mean±s.e.m.) for hyperactivity (A), ataxia (B), irritability (C) and tremor (D) is shown for rats treated with 0 or 10 mg/kg of compound A. Significant difference between compound A and celacol-treated controls was derived from non-parametric analysis (Mann-Whitney U-test, **$p<0.01$,

***p<0.001). Compound A clearly reduced the behavioural symptoms of alcohol withdrawal in each case.

EXAMPLE 6

Effect of Compound A on nicotine withdrawal-induced anxiogenesis in a mouse model Animals Male BKW mice (18–20 g initially) supplied by Bantin and Kingman were housed in groups of 6–8 and allowed access to food and water ad libitum Materials Test compounds were prepared as suspensions in 0.25% celacol (methylcellulose) by ball-milling overnight using a Pascal ball-mill. Further dilution with celacol was carried out as required. Nicotine hydrogen tartrate was prepared as a solution in saline (0.85% w/v NaCl) and doses calculated as base equivalents.

Procedure

Groups of 11 mice were given nicotine (0.1 mg/kg i.p.) twice a day for 1 week and then 2 mg/kg (i.p.) for a second week. 23 hours after the last nicotine dose the mice were given compound A i.p. 1 hour before testing for 5 minutes in a light/dark box, where anxiety is manifested as a tendency to remain in the dark. The proportion of time spent exploring the light side of the box was monitored by video camera. Control mice received chronic saline and acute celacol injections. Statistical analysis was by Analysis of Variance (ANOVA) followed by post-hoc analysis with Bonferroni's test for comparisons among groups.

Figure 6:
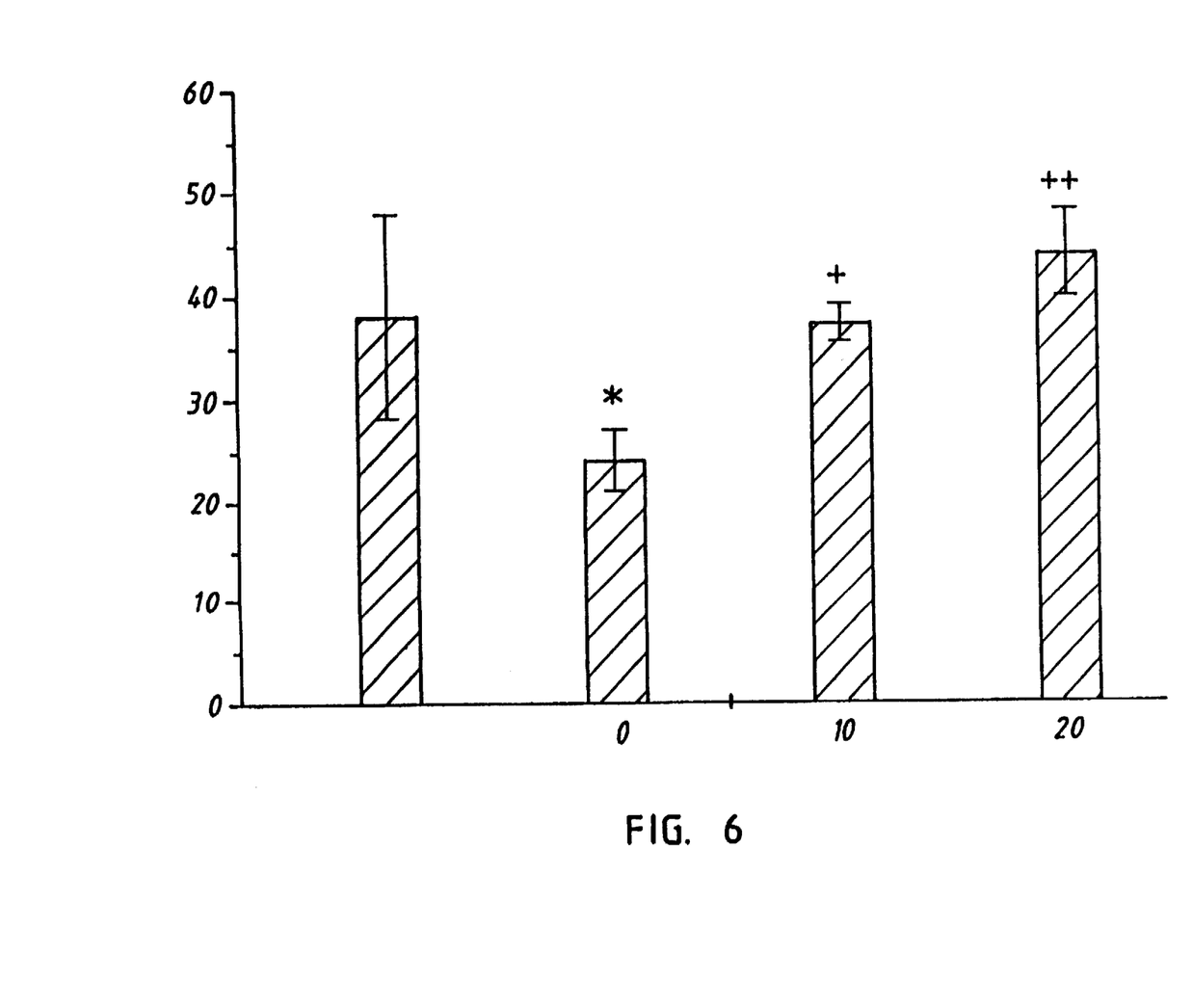
FIG. 6 shows time (%) on the light side of a light/dark box for nicotine-dependant mice given compound A in a single dose of 0, 10 or 20 mg/kg, compared to control mice (C), in the nicotine withdrawal-induced anxiogenesis test of Example 6.

The results are shown in FIG. 6 where the percentage of time on the light side of the box is shown for control mice and for mice withdrawn from nicotine and given a single dose of 0, 10 or 20 mg/kg of compound A (*p<0.05 compared to control; *p<0.05, **p<0.01 compared to nicotine withdrawal).

The results show that treatment with compound A increased the tendency of the animals to spend time on the light side of the box in a dose-dependent manner. Compound A therefore reduced the anxiety which is a symptom of withdrawal from nicotine.

EXAMPLE 7

Effect of compound A on cocaine-induced reverse tolerance in a rat model

Animals

Animals were as described in Example 1, but weighed 180–250 g at the time of use.

Materials

Cocaine hydrochloride was dissolved in 0.85% saline to give the equivalent of 10 mg/kg base. Test compounds were prepared as suspensions as described in Example 1.

Procedure

Compound A (20 mg/kg p.o.), or celacol as control, was given once a day (10.30) 1 hour prior to a dose of cocaine (10 mg/kg, i.p.) or saline as control. On day 8 the animals were placed individually into arenas fitted with photocells connected to a computer which recorded beam crossings to register locomoter activity. Activity scores were recorded for 30 mins commencing 30 mins after oral treatment and for a further 30 mins after administration of saline or cocaine. Treatment group mean and standard error were calculated. Activity scores for animals within each group were compared using non-parametic analysis.

Figure 7:
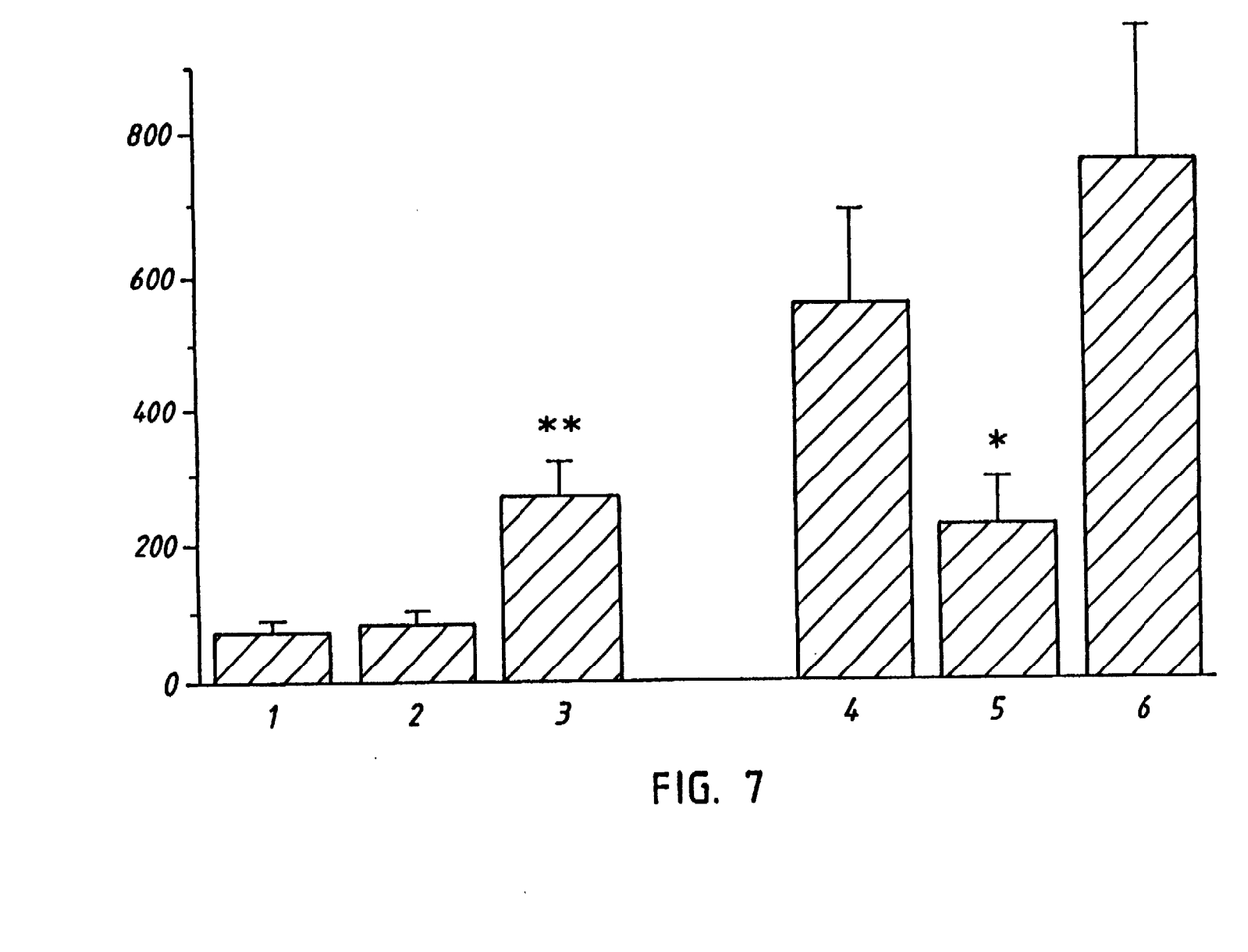
FIG. 7: columns represent activity score (as mean±s.e.m) for rats treated as follows once a day for 8 days in the cocaine-induced reverse tolerance test of Example 7.

The results are set out in FIG. 7, where the columns represent activity scores for the second 30 minutes of measurement. Column 1 represents celacol given as control to saline-treated animals: Column 2 shows that compound A has no effect on normal activity in saline-treated controls. A single dose of cocaine (10 mg/kg) induced significant hyperactivity (third column) in control animals. Cocaine-tolerant animals demonstrated reverse tolerance (fourth column), i.e. were more hyperactive than those given a single dose. Treatment with compound A daily 1 hour before cocaine administration suppressed the development of reverse tolerance (fifth column).

The effect of a single dose of compound A (20 mg/kg p.o.) given 1 hour before cocaine on day 8 to cocaine-tolerant animals is shown in column 6.

EXAMPLE 8

Pharmaceutical Composition

Tablets for oral administration were formulated with the following ingredients:

Compound A . . . 150 mg
Lactose . . . 200 mg
Maize Starch . . . 50 mg
Polyvinylpyrrolidone . . . 4 mg
Magnesium stearate . . . 4 mg The active compound was mixed with the lactose and starch and granulated with a solution of the polyvinylpyrrolidone in water. The resulting granules were dried, mixed with magnesium stearate and compressed to give tablets of average weight 408 mg.

Comparative Example 1

Effect of carbamazepine on alcohol dependence in a withdrawal behavioural syndrome rat model Animals and materials were as described in Example 1.

Procedure

Ethanol (20%, 5 ml per rat p.o.) was given to rats 4 times daily for 7 days. Carbamazepine (40 mg/kg p.o.) or celacol as control was given on 5 occasions, 1 hr before the 3rd dose of ethanol on day 4 and 1 hr before the first and third doses on days 5 and 6.

8–12 hours after the last dose of ethanol the animals were observed on an arena for the behavioural effects of alcohol withdrawal which were scored for severity on an arbitrary scale.

Figure 8:
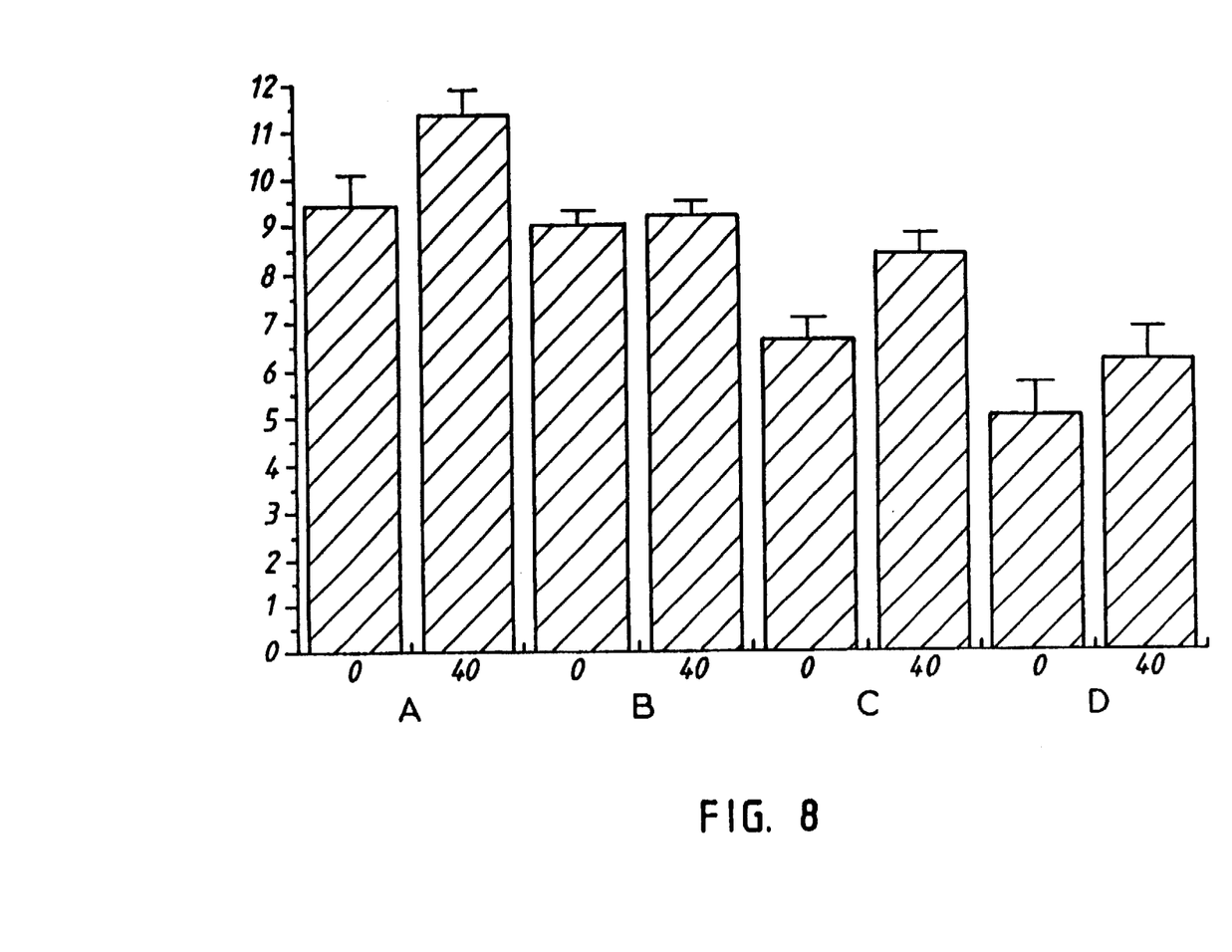
FIG. 8: columns represent activity score (as mean±s.e.m.) for activity (A), ataxia (B), irritability (C) and tremor (D) in rats treated with 0 and 40 mg/kg of carbamazepine in the test of Comparative Example 1.

The results are shown in FIG. 8 where the average score (mean±s.e.m.) for activity (A), ataxia (B), irritability (C) and tremor (D) is shown for rats treated with 0 or 40 mg/kg carbamazepine. The significance of difference between carbamazepine and celacol-treated controls was derived from non-parametric analysis (Mann-Whitney U-test). No effect was significant (p<0.05). The same was observed when the dose of carbamazepine was reduced to 20 mg/kg and to 10 mg/kg. Accordingly carbamazepine does not affect behavioural symptoms provoked by withdrawal from alcohol.

Comparative Example 2

Effect of carbamazepine on the inducation of audiogenic seizures in alcohol-dependent rats Animals and materials were as described in Example 1.

Procedure

Animals were given ethanol (20%, 5 ml per rat p.o.) 4 times daily for 4 days. On day 5, 12 hours after the last does of alcohol, the animals were given carbamazepine (20, 40 or 80 mg/kg) compound A (40 mg/kg) or celacol as control. One hour later the animals were placed individually into a sound-attenuated room and an electric bell was rung for 60 secs (90 decibels). The incidence of seizures within 60 secs for each treatment group was compared to controls using Fischer's exact probability test.

Figure 9:
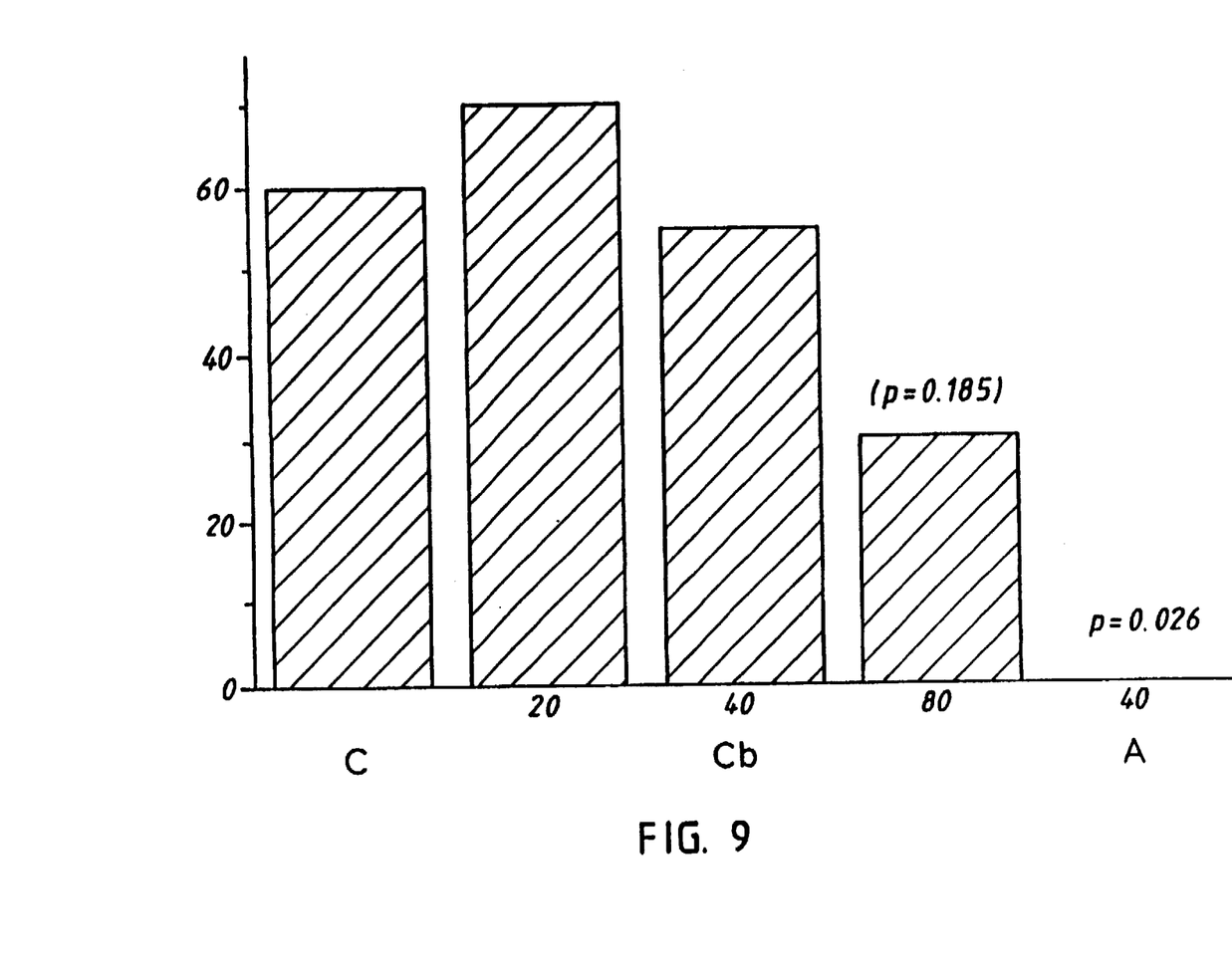
FIG. 9: shows the incidence of audiogenic seizures (as % treated, y axis) in rats given celacol (c), carbamazepine (Cb) at doses of 20, 40 and 80 mg/kg p.o. and compound A at 40 mg/kg p.o. in the test of Comparative Example 2.

The results shown in FIG. 9 indicate that carbamazepine had little significant effect on the incidence of seizures provoked by withdrawal from alcohol.

I claim:

1. A method of (a) preventing or reducing dependence on, or (b) preventing or reducing tolerance or reverse tolerance to, a dependence-inducing agent, the method comprising administering to a human or animal patient in need of such treatment a therapeutically effective amount of a compound selected from 3,5-diamino-6-(2,3-dichlorophenyl)-1,2,4-triazine and the pharmaceutically and veterinarily acceptable acid addition salts thereof, wherein said dependence-inducing agent is selected from the group consisting of opioids, central nervous system depressants, nicotine and tobacco, cannabinoids, psychedelics, arylcyclohexylamines, and inhalants.

2. A method according to claim 1 wherein the compound is administered concomitantly with the dependence-inducing agent.

3. A method according to claim 1 for preventing or reducing dependence on a dependence-inducing agent, which method comprises administering concomitantly with the said compound a second dependence-inducing agent with which the dependence-inducing agent is cross-dependent.

4. A method according to claim 1 wherein the acid addition salt is the salt with isethionic acid.

5. A method according to claim 1 wherein the dependence-inducing agent is an opioid.

6. A method according to claim 3 wherein the opioid is morphine.

7. A method according to claim 1 wherein the dependence-inducing agent is a central nervous system depressant.

8. A method according to claim 5 wherein the central nervous system depressant is ethanol.

9. A method according to claim 1 wherein the dependence-inducing agent is a psychostimulant.

10. A method according to claim 7 wherein the psychostimulant is cocaine.

11. A method according to claim 1 wherein the dependence-inducing agent is nicotine.

* * * * *

UNITED STATES PATENT AND TRADEMARK OFFICE
CERTIFICATE OF CORRECTION

PATENT NO. : 5,801,171
DATED : September 1, 1998
INVENTOR(S) : Nakamura-Craig

It is certified that error appears in the above-identified patent and that said letters patent is hereby corrected as shown below:

Column 11, claim 1, should read as follows:

1. A method of (a) preventing or reducing dependence on, or (b) preventing or reducing tolerance or reverse tolerance to, a dependence-inducing agent, the method comprising administering to a human or animal patient in need of such treatment a therapeutically effective amount of a compound selected from 3,5-diamino-6-(2,3-dichlorophenyl)-1,2,4-triazine and the pharmaceutically and veterinarily acceptable acid addition salts thereof, wherein said dependence-inducing agent is selected from the group consisting of opioids, central nervous system depressants, psychostimulants, nicotine and tobacco, cannabinoids, psychedelics, arylcyclohexylamines, and inhalants.

Signed and Sealed this

Thirty-first Day of August, 1999

*Attest:*

Q. TODD DICKINSON

*Attesting Officer*  *Acting Commissioner of Patents and Trademarks*